US007579478B2

(12) United States Patent
Iera

(10) Patent No.: US 7,579,478 B2
(45) Date of Patent: Aug. 25, 2009

(54) PROCESS FOR THE PURIFICATION OF SUBSTITUTED BENZOXAZOLE COMPOUNDS

(75) Inventor: Silvio Iera, Montreal (CA)

(73) Assignee: Wyeth, Madison, NJ (US)

( * ) Notice: Subject to any disclaimer, the term of this patent is extended or adjusted under 35 U.S.C. 154(b) by 363 days.

(21) Appl. No.: 11/369,113

(22) Filed: Mar. 6, 2006

(65) Prior Publication Data
US 2006/0199967 A1 Sep. 7, 2006

Related U.S. Application Data

(60) Provisional application No. 60/659,212, filed on Mar. 7, 2005.

(51) Int. Cl.
| | | |
|---|---|---|
| C07D 263/56 | (2006.01) |
| C07D 413/00 | (2006.01) |
| C07D 498/00 | (2006.01) |
| C07D 293/00 | (2006.01) |
| C07D 421/00 | (2006.01) |
| C07D 517/00 | (2006.01) |

(52) U.S. Cl. ................ 548/224; 548/100; 548/215; 548/217; 548/237
(58) Field of Classification Search ............ 548/178, 548/224, 310.7, 146, 148, 152, 215, 217, 548/237, 300.1, 301.7, 302.7, 304.4, 100; 514/228.8, 394, 183, 359, 365, 367, 374, 514/385
See application file for complete search history.

(56) References Cited

U.S. PATENT DOCUMENTS

| 6,794,403 B2 | 9/2004 | Malamas et al. |
| 2006/0199852 A1 * | 9/2006 | Iera ............................ 514/375 |

FOREIGN PATENT DOCUMENTS

WO   WO 03/050095   *   6/2003

OTHER PUBLICATIONS

U.S. Appl. No. 11/368,719, Iera, Silvio.*
U.S. Appl. No. 60/336,663, Malamas et al.*
Armarego, W.L.F.; Perrin, D.D. (1997). Purification of Laboratory Chemicals (4th Edition). Elsevier. Online version available at http://www.knovel.com/knovel2/Toc.jsp?BookID=489&VerticalID=0.*
"Melting Point." Retrieved online via the Internet [Jun. 19, 2008] URL: http://en.wikipedia.org/wiki/Melting_point.*
Al-Azzawi "The menopause and its treatment in perspective," *Postgraduate Medical Journal* (2001) 77:292-304.
Bhat et al., "A novel human estrogen receptor beta: identification and functional analysis of additional N-terminal amino acids," *Journal of Steroid Biochemistry & Molecular Bilogy* (1998) 67(3):233-240.
Brincat "Hormone replacement therapy and the skin," *Maturitas* (2000) 35(2):107-117.

Calvin "Oestrogens and wound healing," *Maturitas* (2000) 34(3):195-210.
Couse et al., "Tissue distribution and quantitative analysis of estrogen receptor-alpha (ERalpha) and estrogen receptor-beta (ERbeta) messenger ribonucleic acid in the wild-type and ERalpha-knockout mouse," *Endocrinology* (1997) 138(11):4613-4621.
Cowley et al., "Estrogen receptors alpha and beta form heterodimers on DNA" *Journal of Biological Chemistry* (1997) 272(32):19858-19862.
Crandall, "Estrogen replacement therapy and colon cancer: a clinical review," *Journal of Womens Health & Gender Based Medicine* (1999) 8(9):1155-1166.
Epperson et al., "Gonadal steroids in the treatment of mood disorders," *Psychosomatic Medicine* (1999) 61:676(5)-697.
Finking et al., "[The effects of estrogen in the cardiovascular system]," *Zeitschrift fur Kardiologie* (2000) 89:442-443.
Fitzpatrick et al., "Expression of estrogen receptor-beta protein in rodent ovary," *Endocrinology* (1999) 140(6):2581-2591.
Goldstein et al., "A pharmacological review of selective oestrogen receptor modulators," *Human Reproduction Update* (2000) 6(3)212-224.
Green et al., "Human oestrogen receptor cDNA: sequence, expression and homology to v-erb-A," *Nature* (1986) 320(6058)134-139.
Hall et al., "The multifaceted mechanisms of estradiol and estrogen receptor signaling," *Journal of Biological Chemistry* (2001) 276(40):36869-36872.
Hurn et al., "Estrogen as a neuroprotectant in stroke," *Journal of Cerebral Blood Flow & Metabolism* (2000) 20(4):631-652.
Kuiper et al., "Cloning of a novel receptor expressed in rat prostate and ovary," *Proceedings of the Natural Academy of Sciences of the USA* (1996) 93(12):5925-5930.
Kuiper et al., "Comparison of the ligand binding specificity and transcript tissue distribution of estrogen receptors alpha and beta," *Endocrinology* (1997) 138(3):863-870.
Levin et al., "Cell localization, physiology, and nongenomic actions of estrogen receptors," *Journal of Applied Physiology* (2001) 91(4):1860-1867.
Levin et al., "Cellular Functions of the Plasma Membrane Estrogen Receptor," *Trends in Endocrinology & Metabolism* (1999) 10(9):374-377.

(Continued)

*Primary Examiner*—Kamal A Saeed
*Assistant Examiner*—Samantha L Shterengarts
(74) *Attorney, Agent, or Firm*—Pepper Hamilton LLP

(57) ABSTRACT

The present invention provides processes for the purification of substituted benzoxazole compounds, and in particular 2-(3-fluoro-4-hydroxy-phenyl)-7-vinyl-benzooxazol-5-ol. The processes include recrystallizing the compound from a solution comprising acetone and acetonitrile; treating the crude purified product with a clarifying agent in a solution comprising ethyl acetate, and precipitating or triturating the compound from a mixed solvent system.

24 Claims, No Drawings

OTHER PUBLICATIONS

McDonnell *Principles of Molecular Regulation* (2000) pp. 351-361.

McDonnell "Selective estrogen receptor modulators (SERMs): A first step in the development of perfect hormone replacement therapy regimen," *Journal of the Society for Gynecologic Investigation* (2000) 7(1 Suppl):S10-S15.

McKenna et al., "Nuclear receptor coregulators: cellular and molecular biology," *Endocrine Reviews* (1999) 20(3):321-344.

Mendelsohn et al., "The protective effects of estrogen on the cardiovascular system," *New England Journal of Medicine* (1999) 340(23):1801-1811.

Moggs et al., "Estrogen receptors: orchestrators of pleiotropic cellular responses," *EMBO Reports* (2001) 2(9):775-781.

Monk et al., "Use of estrogens for the prevention and treatment of Alzheimer's disease," *Dementia & Geriatric Cognitive Disorders* (2000) 11(1):1-10.

Paige et al., "Estrogen receptor (ER) modulators each induce distinct conformational changes in ER alpha and ER beta," *Proceedings of the National Academy of Sciences of the USA* (1999) 96(7):3999-4004.

Pelzer et al., "Estrogen effects in the myocardium: inhibition of NF-kappaB DNA binding by estrogen receptor-alpha and -beta," *Biochemical & Biophysical Research Communications* (2001) 286(5):1153-1157.

Pike et al., "Structure of the ligand-binding domain of oestrogen receptor beta in the presence of a partial agonist and a full antagonist," *EMBO* (1999) 18(17):4608-4618.

Quaedackers et al., "4-hydroxytamoxifen trans-represses nuclear factor-kappa B activity in human osteoblastic U2-OS cells through estrogen receptor (ER)alpha, and not through ER beta," (2001) 142(3):1156-1166.

Raggon et al., "A Reliable Multikilogram-Scale Synthesis of 2-Acetamido-5-Vinylpyridine Using Catalytic BINAP in a Modified Heck Reaction," *Organic Process Search & Development* (2002) 6(1):67-69.

Sar et al., "Differential expression of estrogen receptor-beta and estrogen receptor-alpha in the rat ovary," *Endocrinology* (1999) 140(2):963-971.

Shiau et al., "The structural basis of estrogen receptor/coactivator recognition and the antagonism of this interaction by tamoxifen," *Cell* (1998) 95(7):927-937.

Heinenberg et al., "Polymeric nitrons. 2. Synthesis, irradiation and waveguide mode spectroscopy of polymeric nitrons derived from polymeric benzaldehydes and n-isoprophylhydroxylamine," *Macromolecules* (2000) 35(9):3448-3455.

Gibson et al., "Highly efficient C-C coupling reactions using metallated benzylphosphine compexes of palladium," *Chemical Communications* (2001) pp. 779-780.

Malamas et al., "Design and synthesis of aryl diphenolic azoles as potent and selective estrogen receptor-β Ligands," *J Med Chem* (2004) 47:5021-5040.

* cited by examiner

US 7,579,478 B2

PROCESS FOR THE PURIFICATION OF SUBSTITUTED BENZOXAZOLE COMPOUNDS

This application claims benefit of priority to U.S. provisional patent application Ser. No. 60/659,212 filed on Mar. 7, 2005, which is hereby incorporated in its entirety.

FIELD OF THE INVENTION

The present invention relates to processes for the purification of substituted benzoxazole compounds, and in particular 2-(3-fluoro-4-hydroxy-phenyl)-7-vinyl-benzooxazol-5-ol. The processes include recrystallizing the compound from a solution comprising acetone and acetonitrile; treating the crude purified product with a clarifying agent in a solution comprising ethyl acetate, and precipitating or triturating the compound from a mixed solvent system.

BACKGROUND OF THE INVENTION

The pleiotropic effects of estrogens in mammalian tissues have been well documented, and it is now appreciated that estrogens affect many organ systems [Mendelsohn and Karas, New England Journal of Medicine 340: 1801-1811 (1999), Epperson, et al., Psychosomatic Medicine 61: 676-697 (1999), Crandall, Journal of Womens Health & Gender Based Medicine 8: 1155-1166 (1999), Monk and Brodaty, Dementia & Geriatric Cognitive Disorders 11: 1-10 (2000), Hurn and Macrae, Journal of Cerebral Blood Flow & Metabolism 20: 631-652 (2000), Calvin, Maturitas 34: 195-210 (2000), Finking, et al., Zeitschrift fur Kardiologie 89: 442-453 (2000), Brincat, Maturitas 35: 107-117 (2000), Al-Azzawi, Postgraduate Medical Journal 77: 292-304 (2001)]. Estrogens can exert effects on tissues in several ways, and the most well characterized mechanism of action is their interaction with estrogen receptors leading to alterations in gene transcription. Estrogen receptors are ligand-activated transcription factors and belong to the nuclear hormone receptor superfamily. Other members of this family include the progesterone, androgen, glucocorticoid and mineralocorticoid receptors. Upon binding ligand, these receptors dimerize and can activate gene transcription either by directly binding to specific sequences on DNA (known as response elements) or by interacting with other transcription factors (such as AP1), which in turn bind directly to specific DNA sequences [Moggs and Orphanides, EMBO Reports 2: 775-781 (2001), Hall, et al., Journal of Biological Chemistry 276: 36869-36872 (2001), McDonnell, Principles Of Molecular Regulation. p351-361 (2000)]. A class of "coregulatory" proteins can also interact with the ligand-bound receptor and further modulate its transcriptional activity [McKenna, et al., Endocrine Reviews 20: 321-344 (1999)]. It has also been shown that estrogen receptors can suppress NFκB-mediated transcription in both a ligand-dependent and independent manner [Quaedackers, et al., Endocrinology 142: 1156-1166 (2001), Bhat, et al., Journal of Steroid Biochemistry & Molecular Biology 67: 233-240 (1998), Pelzer, et al., Biochemical & Biophysical Research Communications 286: 1153-7 (2001)].

Estrogen receptors can also be activated by phosphorylation. This phosphorylation is mediated by growth factors such as EGF and causes changes in gene transcription in the absence of ligand [Moggs and Orphanides, EMBO Reports 2: 775-781 (2001), Hall, et al., Journal of Biological Chemistry 276: 36869-36872 (2001)].

A less well-characterized means by which estrogens can affect cells is through a so-called membrane receptor. The existence of such a receptor is controversial, but it has been well documented that estrogens can elicit very rapid non-genomic responses from cells. The molecular entity responsible for transducing these effects has not been definitively isolated, but there is evidence to suggest it is at least related to the nuclear forms of the estrogen receptors [Levin, Journal of Applied Physiology 91: 1860-1867 (2001), Levin, Trends in Endocrinology & Metabolism 10: 374-377 (1999)].

Two estrogen receptors have been discovered to date. The first estrogen receptor was cloned about 15 years ago and is now referred to as ERα [Green, et al., Nature 320: 134-9 (1986)]. The second form of the estrogen receptor was found comparatively recently and is called ERβ [Kuiper, et al., Proceedings of the National Academy of Sciences of the United States of America 93: 5925-5930 (1996)]. Early work on ERβ focused on defining its affinity for a variety of ligands and indeed, some differences with ERα were seen. The tissue distribution of ERβ has been well mapped in the rodent and it is not coincident with ERα. Tissues such as the mouse and rat uterus express predominantly ERα, whereas the mouse and rat lung express predominantly ERβ [Couse, et al., Endocrinology 138: 4613-4621 (1997), Kuiper, et al., Endocrinology 138: 863-870 (1997)]. Even within the same organ, the distribution of ERα and ERβ can be compartmentalized. For example, in the mouse ovary, ERβ is highly expressed in the granulosa cells and ERα is restricted to the thecal and stromal cells [Sar and Welsch, Endocrinology 140: 963-971 (1999), Fitzpatrick, et al., Endocrinology 140: 2581-2591 (1999)]. However, there are examples where the receptors are coexpressed and there is evidence from in vitro studies that ERα and ERβ can form heterodimers [Cowley, et al., Journal of Biological Chemistry 272: 19858-19862 (1997)].

A large number of compounds have been described that either mimic or block the activity of 17β-estradiol. Compounds having roughly the same biological effects as 17β-estradiol, the most potent endogenous estrogen, are referred to as "estrogen receptor agonists". Those which, when given in combination with 17β-estradiol, block its effects are called "estrogen receptor antagonists". In reality there is a continuum between estrogen receptor agonist and estrogen receptor antagonist activity and indeed some compounds behave as estrogen receptor agonists in some tissues and estrogen receptor antagonists in others. These compounds with mixed activity are called selective estrogen receptor modulators (SERMS) and are therapeutically useful agents (e.g. EVISTA) [McDonnell, Journal of the Society for Gynecologic Investigation 7: S10-S15 (2000), Goldstein, et al., Human Reproduction Update 6: 212-224 (2000)]. The precise reason why the same compound can have cell-specific effects has not been elucidated, but the differences in receptor conformation and/or in the milieu of coregulatory proteins have been suggested.

It has been known for some time that estrogen receptors adopt different conformations when binding ligands. However, the consequence and subtlety of these changes has been only recently revealed. The three dimensional structures of ERα and ERβ have been solved by co-crystallization with various ligands and clearly show the repositioning of helix 12 in the presence of an estrogen receptor antagonist which sterically hinders the protein sequences required for receptor-coregulatory protein interaction [Pike, et al., Embo 18: 4608-4618 (1999), Shiau, et al., Cell 95: 927-937 (1998)]. In addition, the technique of phage display has been used to identify peptides that interact with estrogen receptors in the presence of different ligands [Paige, et al., Proceedings of the National Academy of Sciences of the United States of America 96: 3999-4004 (1999)]. For example, a peptide was identified that distinguished between ERα bound to the full estrogen receptor agonists 17β-estradiol and diethylstilbesterol. A different peptide was shown to distinguish between clomiphene bound to ERα and ERβ. These data indicate that each ligand potentially places the receptor in a unique and unpredictable conformation that is likely to have distinct biological activities.

As mentioned above, estrogens affect a panoply of biological processes. In addition, where gender differences have been described (e.g. disease frequencies, responses to challenge, etc), it is possible that the explanation involves the difference in estrogen levels between males and females.

U.S. Pat. No. 6,794,403, incorporated herein by reference in its entirety, describes the preparation of substituted benzoxazole ERβ selective ligands having the Formula I, infra. Given the importance of these compounds as potential therapeutics, it can be seen that improved processes for their purification are of great value. This invention is directed to these, as well as other, important ends.

SUMMARY OF THE INVENTION

In one aspect, the present invention provides processes for the purification of compounds of Formula I:

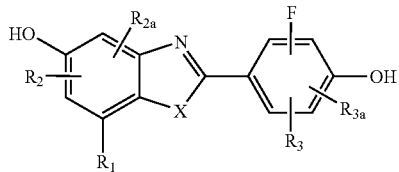

I wherein:

$R_1$ is alkenyl of 2-7 carbon atoms; wherein the alkenyl moiety is optionally substituted with one or more substituents independently selected from hydroxyl, —CN, halogen, trifluoroalkyl, trifluoroalkoxy, —$COR_5$, —$CO_2R_5$, —$NO_2$, $CONR_5R_6$, $NR_5R_6$ and $N(R_5)COR_6$;

$R_2$ and $R_{2a}$ are each, independently, hydrogen, hydroxyl, halogen, alkyl of 1-6 carbon atoms, alkoxy of 1-4 carbon atoms, alkenyl of 2-7 carbon atoms, alkynyl of 2-7 carbon atoms, trifluoroalkyl of 1-6 carbon atoms, or trifluoroalkoxy of 1-6 carbon atoms; wherein the alkyl, alkenyl, or alkynyl moieties are each optionally substituted with one or more substituents independently selected from hydroxyl, —CN, halogen, trifluoroalkyl, trifluoroalkoxy, —$COR_5$, —$CO_2R_5$, —$NO_2$, $CONR_5R_6$, $NR_5R_6$ and $N(R_5)COR_6$;

$R_3$, and $R_{3a}$ are each, independently, hydrogen, alkyl of 1-6 carbon atoms, alkenyl of 2-7 carbon atoms, alkynyl of 2-7 carbon atoms, halogen, alkoxy of 1-4 carbon atoms, trifluoroalkyl of 1-6 carbon atoms, or trifluoroalkoxy of 1-6 carbon atoms; wherein the alkyl, alkenyl, or alkynyl moieties are each optionally substituted with one or more substituents independently selected from hydroxyl, —CN, halogen, trifluoroalkyl, trifluoroalkoxy, —$COR_5$, —$CO_2R_5$, —$NO_2$, $CONR_5R_6$, $NR_5R_6$ and $N(R_5)COR_6$;

$R_5$, $R_6$ are each, independently, hydrogen, alkyl of 1-6 carbon atoms, aryl of 6-10 carbon atoms;

X is O, S, or $NR_7$; and $R_7$ is hydrogen, alkyl of 1-6 carbon atoms, aryl of 6-10 carbon atoms, —$COR_5$, —$CO_2R_5$ or —$SO_2R_5$;

from a mixture comprising the compound and at least one impurity. In some embodiments, the processes include the steps of:

a) recrystallizing said compound from a solution comprising acetone and acetonitrile to provide a crude purified product;

b) dissolving said crude purified product in a solution comprising ethyl acetate;

c) treating said solution comprising ethyl acetate with a clarifying agent to form a clarified solution;

d) optionally concentrating said clarified solution to form a concentrated clarified solution or slurry;

e) adding a nonpolar solvent to said clarified solution or said clarified concentrated solution or slurry to form a mixed solvent solution or slurry; and f) collecting the purified compound from said mixed solvent solution or slurry.

In some embodiments of the methods of the invention X is O. In further such embodiments, X is O and $R_1$ is alkenyl of 2-3 carbon atoms, which is optionally substituted with hydroxyl, —CN, halogen, trifluoroalkyl, trifluoroalkoxy, —$COR_5$, —$CO_2R_5$, —$NO_2$, $CONR_5R_6$, $NR_5R_6$ or $N(R_5)COR_6$. In still further such embodiments, the compound is 2-(3-fluoro-4-hydroxyphenyl)-7-vinyl-1,3-benzoxazol-5-ol.

DETAILED DESCRIPTION OF THE INVENTION

The present invention provides processes for the purification of a compound of Formula I:

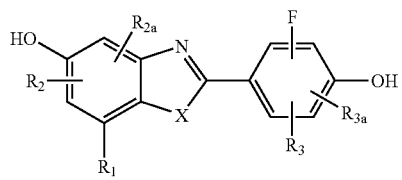

I wherein:

$R_1$ is alkenyl of 2-7 carbon atoms; wherein the alkenyl moiety is optionally substituted with one or more substituents independently selected from hydroxyl, —CN, halogen, trifluoroalkyl, trifluoroalkoxy, —$COR_5$, —$CO_2R_5$, —$NO_2$, $CONR_5R_6$, $NR_5R_6$ and $N(R_5)COR_6$;

$R_2$ and $R_{2a}$ are each, independently, hydrogen, hydroxyl, halogen, alkyl of 1-6 carbon atoms, alkoxy of 1-4 carbon atoms, alkenyl of 2-7 carbon atoms, alkynyl of 2-7 carbon atoms, trifluoroalkyl of 1-6 carbon atoms, or trifluoroalkoxy of 1-6 carbon atoms; wherein the alkyl, alkenyl, or alkynyl moieties are each optionally substituted with one or more substituents independently selected from hydroxyl, —CN, halogen, trifluoroalkyl, trifluoroalkoxy, —$COR_5$, —$CO_2R_5$, —$NO_2$, $CONR_5R_6$, $NR_5R_6$ and $N(R_5)$ $COR_6$;

$R_3$, and $R_{3a}$ are each, independently, hydrogen, alkyl of 1-6 carbon atoms, alkenyl of 2-7 carbon atoms, alkynyl of 2-7 carbon atoms, halogen, alkoxy of 1-4 carbon atoms, trifluoroalkyl of 1-6 carbon atoms, or trifluoroalkoxy of 1-6 carbon atoms; wherein the alkyl, alkenyl, or alkynyl moieties are each optionally substituted with one or more substituents independently selected from hydroxyl, —CN, halogen, trifluoroalkyl, trifluoroalkoxy, —$COR_5$, —$CO_2R_5$, —$NO_2$, $CONR_5R_6$, $NR_5R_6$ and $N(R_5)COR_6$;

R$_5$, R$_6$ are each, independently, hydrogen, alkyl of 1-6 carbon atoms, aryl of 6-10 carbon atoms;

X is O, S, or NR$_7$; and

R$_7$ is hydrogen, alkyl of 1-6 carbon atoms, aryl of 6-10 carbon atoms, —COR$_5$, —CO$_2$R$_5$ or —SO$_2$R$_5$;

from a mixture comprising said compound and at least one impurity, comprising the steps of:

a) recrystallizing said compound from a solution comprising acetone and acetonitrile to provide a crude purified product;

b) dissolving said crude purified product in a solution comprising ethyl acetate;

c) treating said solution comprising ethyl acetate with a clarifying agent to form a clarified solution;

d) optionally concentrating said clarified solution to form a concentrated clarified solution or slurry;

e) adding a nonpolar solvent to said clarified solution or said clarified concentrated solution or slurry to form a mixed solvent solution or slurry; and f) collecting the purified compound from said mixed solvent solution or slurry.

In some embodiments of the methods of the invention X is O. In further such embodiments, X is O and R$_1$ is alkenyl of 2-3 carbon atoms, which is optionally substituted with hydroxyl, —CN, halogen, trifluoroalkyl, trifluoroalkoxy, —COR$_5$, —CO$_2$R$_5$, —NO$_2$, CONR$_5$R$_6$, NR$_5$R$_6$ or N(R$_5$)COR$_6$. In still further such embodiments, the compound has the Formula:

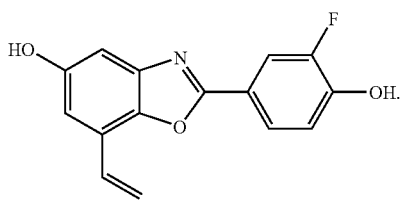

In some embodiments, R$_1$ is suitably an optionally substituted alkene of 2-3 carbon atoms. In some embodiments, R$_1$ is vinyl. In some embodiments, R$_2$, R$_{2a}$, R$_3$, R$_{3a}$ are each independently suitably hydrogen. In certain embodiments R$_2$, R$_{2a}$, R$_3$ and R$_{3a}$ are all hydrogen.

The processes described herein are useful for the purification of compounds of Formula I, and especially for the purification of 2-(3-fluoro-4-hydroxyphenyl)-7-vinyl-1,3-benzoxazol-5-ol. Generally, the processes will be applied to a crude preparation of the compound, for example a crude synthetic preparation, which contains one or more impurities.

In accordance with the present processes, the crude product is first recrystallized from a solution containing acetone and acetonitrile as the two major solvent components of the solution. In some embodiments, the solution is composed of acetone and acetonitrile.

In one nonlimiting embodiment, the crude compound is dissolved in acetone to form a solution; and acetonitrile is added to the solution to form a second solution from which the compound is to be crystallized. The dissolving of the crude compound in the acetone solution is beneficially accomplished at an elevated temperature, generally greater than about 25° C., preferably greater than about 50° C., for example from about 50° C. to about 60° C. Although any convenient amount of acetone can be employed that is sufficient to dissolve the compound, generally, about 0.75 to about 0.9 liters of acetone, preferably about 0.82 liters of acetone, is employed for each 100 grams of dry crude compound. Thus, about 1.6 to about 2.0 liters of acetone, preferably about 1.8 liters of acetone, would be employed for each 219 grams of dry crude compound.

After the compound is dissolved, in the acetone solution, a solution including acetonitrile as its major component is added. In some preferred embodiments, neat acetonitrile is added. Any convenient amount of acetonitrile can be added to the solution that is effective to provide an acceptable yield. In some preferred embodiments, the volume of acetonitrile added is from about 30% to about 70%, or about 40% to about 65%, or from about 48% to about 55%, of the volume of the solution of the compound dissolved in acetone. More preferably, the volume of acetonitrile added is about equal to the volume of the acetone solution.

Preferably, the addition of the acetonitrile solution is performed while maintaining the elevated temperature. The addition can be performed over any convenient time, for example over about 30 minutes.

In some embodiments, the resulting solution containing acetone, acetonitrile and the dissolved compound is then concentrated, preferably to about one half its volume, and also preferably while maintaining the elevated temperature. Any convenient means can be used to concentrate the solution, for example distillation at atmospheric pressure.

The resulting concentrated solution is then cooled to crystallize the product. For example, the solution can be cooled to about −10° C. to about 10° C., preferably from −3° C. to about 3° C. It is generally advantageous to hold the solution at the cool temperature for a period of time after the cooling is complete, to afford maximal yield of product. Generally, holding the solution at −10° C. to about 10° C., preferably from −3° C. to about 3° C., for about an hour or longer, for example about 90 minutes, is sufficient.

In some embodiments, is can be advantageous to cool the solution in more than one stage. For example, in some embodiments, the concentrated solution is first cooled to an intermediate temperature, for example from about 45° C. to about 50° C., and is then held at that temperature for a period of time, before cooling to lower temperature as described above. Generally, holding the solution at the intermediate temperature for about ten minutes or longer, about twenty minutes or longer, about thirty minutes or longer, or about 45 minutes or longer, is sufficient. Preferably, the solution is held at an intermediate temperature of from about 50° C. to about 60° C., more preferably from about 45° C. to about 50° C., for about thirty minutes.

After cooling is complete, the crude purified product can be collected by any convenient means, for example by filtering the solution. The crude purified product can then be washed (for example with one or more treatments with precooled acetonitrile), and then dried by standard procedures, for example at 55° C. to about 60° C., under vacuum.

The crude purified product obtained from the recrystallization is then dissolved in a suitable solvent, and the resulting solution is clarified by treatment with a clarifying agent; i.e., a clarifying agent is added to the solution, and then physically removed, for example by filtration. Any of the many such agents that are known to be useful for adsorbing impurities in synthetic purification regimes can be employed. In one preferred embodiment, the clarifying agent is charcoal.

Generally, the crude purified product is dissolved in ethyl acetate to form an ethyl acetate solution. Generally, the crude purified product is dissolved in about 18 to about 28 volumes of ethyl acetate, preferably about 23 volumes of ethyl acetate, preferably at elevated temperature, for example from about 70° C. to about 90° C., preferably from about 75° C. to about 80° C.

In some embodiments, the ethyl acetate solution is cooled back to a lower temperature, for example to about 25° C. to about 45° C. before the clarifying agent is added.

Generally the clarifying agent, preferably charcoal, is added to the ethyl acetate solution in an amount of about 4 to about 5 grams per liter of ethyl acetate solution, preferably about 4.4 grams per liter of ethyl acetate solution. The mixture is stirred for about 0.5 hour, and the mixture is then filtered to yield a clarified solution.

In some embodiments, the clarified solution is then concentrated, preferably to about 5 volumes to about 10 volumes relative to the volume of the crude purified product. The clarified solution can be concentrated by a variety of standard procedures. Preferably, the concentration is performed at atmospheric pressure, for example by distillation. During the concentration, the compound can start to precipitate out of solution, forming a slurry.

A nonpolar solvent is then added to the concentrated solution or slurry to form a mixed solvent solution or slurry. Preferably, the nonpolar solvent is added in an amount that is about 4 to about 8 volumes relative to the volume of the crude purified product. Preferably, the nonpolar solvent is added while maintaining the solution or slurry at elevated temperature, for example about 75° C. to about 85° C. A variety of nonpolar solvents can be employed, including hydrocarbon solvents of suitable boiling point, for example heptane, and ethers. One preferred solvent is heptane.

The purified product is then collected from the mixed solvent solution or slurry by cooling and physical separation of the solid product form the solution. Generally, the mixed solvent solution or slurry is then cooled to complete crystallization of the product. For example, the solution can be cooled to about 0° C. to about 5° C. It is generally advantageous to hold the solution at the cool temperature for a period of time after the cooling is complete, to afford maximal yield of product. Generally, holding the solution at 0° C. to about 5° C., for about an hour or longer, for example up to about 90 minutes, is sufficient.

In some embodiments, is can be advantageous to cool the solution in more than one stage. For example, in some embodiments, the mixed solvent solution or slurry is first cooled to an intermediate temperature, for example from about 45° C. to about 50° C., and is then held at that temperature for a period of time, before cooling to lower temperature as described above. Generally, holding the solution at the intermediate temperature for about ten minutes or longer, about twenty minutes or longer, about thirty minutes or longer, or about 45 minutes or longer is sufficient. Preferably, the solution is held at an intermediate temperature of from about 50° C. to about 60° C., more preferably from about 45° C. to about 50° C., for about thirty minutes.

After cooling is complete, the crude purified product can be collected by any convenient means, for example by filtering the solution. The crude purified product can then be dried by standard procedures, for example at 55° C. to about 65° C., under vacuum, to afford the purified compound.

The processes of the invention provide products of high purity, for example purity of about 99.0% or greater, about 99.2% or greater, or about 99.4% or greater.

The processes of the invention typically provide recoveries of compound (relative to the crude product starting material) of 80% or greater, 83% or greater, 86% or greater, or 89% or greater.

The present invention also provides products of the process of the described herein, having purity of about 99.0% or greater, about 99.2% or greater, or about 99.4% or greater.

As used herein, the term "alkyl" or "alkylene" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, butenyl, pentenyl, hexenyl, butadienyl, pentadienyl, hexadienyl, and the like.

As used herein, "alkynyl" refers to an alkyl group having one or more triple carbon-carbon bonds. Example alkynyl groups include ethynyl, propynyl, butynyl, pentynyl, and the like.

As used herein, "halo" or "halogen" refers to fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "aryl" refers to a 6 to 10 membered mono or bicyclic aromatic group, for example, phenyl or naphthyl.

As used herein, "trifluoroalkyl" refers to an alkyl group substituted by three fluorine atoms. A trifluoroalkyl group can contain from 1 to about 20, from 2 to about 20, from 1 to about 10, from 1 to about 8, from 1 to about 6, from 1 to about 4, or from 1 to about 3 carbon atoms. One example of trifluoroalkyl is trifluoromethyl.

As used herein, "trifluoroalkoxy" refers to an alkoxy group substituted by three fluorine atoms. A trifluoroalkoxy group can contain from 1 to about 20, from 2 to about 20, from 1 to about 10, from 1 to about 8, from 1 to about 6, from 1 to about 4, or from 1 to about 3 carbon atoms. One example of trifluoroalkoxy is trifluoromethoxy.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl and $C_6$ alkyl.

The compounds of the present invention can contain an asymmetric atom, and some of the compounds can contain one or more asymmetric atoms or centers, which can thus give rise to optical isomers (enantiomers) and diastereomers. The present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The processes described herein can be carried out in air or under an inert atmosphere. Typically, the processes are carried out in air.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The processes of this invention are suitable for the purification of compounds Formula I on any convenient scale, for example greater than about 0.01 mg, 0.10 mg, 1 mg, 10 mg, 100 mg, 1 g, 10 g, 100 g, 1 kg, 10 kg or more. The processes are particularly advantageous for the large scale (e.g., greater than about ten gram) purification.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of 2-(3-Fluoro-4-hydroxyphenyl)-7-vinylbenzooxazol-5-ol

A 2 gallon hydrogenator was charged with 2-(3-Fluoro-4-hydroxyphenyl)-7-bromobenzooxazol-5-ol (300 g, 0.926 mole), tri-o-tolylphosphine (9.1 g, 3.3%), palladium diacetate (2.1 g 1%), acetonitrile (4.5 L), and triethylamine (375 g, 4 eq). The hydrogenator was flushed with nitrogen, and with ethylene; and then the pressure was adjusted to 50 psi. The reaction mixture was heated to 75° C. and held for 16 hours, at which time HPLC sampling indicated 0.2% of starting material remaining. The mixture was cooled to 35-40° C. and filtered through a 0.2μ cartridge, and washed with 1,2-diethoxyethane (1.2 L). The filtrate was concentrated under vacuum to 1.2 L, and water (1.5 L) and 1,2-diethoxyethane (1.2 L) were added. The pH was adjusted to 11-12 by adding 1.4 L of 2N NaOH at 15-20° C. The phases were separated, and the organic phase was extracted with water (300 ml), and 2 N NaOH (20 mL). The combined aqueous phase was washed with 1,2-diethoxyethane (2×900 mL). The pH was adjusted to 2.5-3.5 by adding 500 mL of 4N HCl at 15-20° C. After holding for 4 hours, the solid was filtered off and washed with water (3×200 mL).

The wet cake was suspended in acetone (1822 mL) and heated to 54-60° C. then held for complete solution. While maintaining at 54-60° C. acetonitrile was added (1822 mL) over 0.5 hour. The solution was concentrated by distilling at atmospheric pressure to a volume of 1.8-2.0 L, then the concentrate was cooled to 45-50° C. and held for 0.5 hour; then cooled to −3 to 3° C. and held for 1 hour. The solid was filtered off and washed with precooled acetonitrile (2×200 mL); then dried in a vacuum oven at 55-65° C. and 5-10 mm Hg for 24 hours to give 180 g (71.5% yield) of product.

The product from above was dissolved in ethyl acetate (23 volumes) at 75-80° C. The resulting solution was cooled back to 25-45° C. and treated with charcoal. The filtrate was then concentrated at atmospheric pressure to 7 volumes, and to the slurry was added heptane (6 volumes) while maintaining at 75-80° C. The solution was then cooled to 45-50° C., held for 0.5 hour, then cooled to 0-5° C., and held for 1 hour. The solid was filtered off, dried at 55-65° C., 5-10 mmHg, to afford an 87% recovery and 99.4% purity.

As those skilled in the art will appreciate, numerous changes and modifications may be made to the preferred embodiments of the invention without departing from the spirit of the invention.

It is intended that all such variations fall within the scope of the invention. It is intended that each of the patents, applications, and printed publications including books mentioned in this patent document be hereby incorporated by reference in their entirety.

What is claimed is:

1. A process for purifying a compound of Formula I:

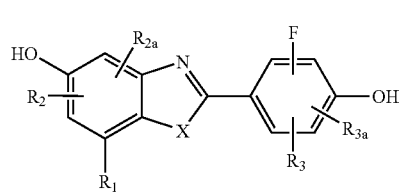

wherein:
$R_1$ is alkenyl of 2-7 carbon atoms; wherein the alkenyl moiety is optionally substituted with one or more substituents independently selected from hydroxyl, —CN, halogen, trifluoroalkyl, trifluoroalkoxy, —COR$_5$, —CO$_2$R$_5$, —NO$_2$, CONR$_5$R$_6$, NR$_5$R$_6$ and N(R$_5$)COR$_6$;

$R_2$ and $R_{2a}$ are each, independently, hydrogen, hydroxyl, halogen, alkyl of 1-6 carbon atoms, alkoxy of 1-4 carbon atoms, alkenyl of 2-7 carbon atoms, alkynyl of 2-7 carbon atoms, trifluoroalkyl of 1-6 carbon atoms, or trifluoroalkoxy of 1-6 carbon atoms; wherein the alkyl, alkenyl, or alkynyl moieties are each optionally substituted with one or more substituents independently selected from hydroxyl, —CN, halogen, trifluoroalkyl, trifluoroalkoxy, —COR$_5$, —CO$_2$R$_5$, —NO$_2$, CONR$_5$R$_6$, NR$_5$R$_6$ and N(R$_5$)COR$_6$;

$R_3$, and $R_{3a}$ are each, independently, hydrogen, alkyl of 1-6 carbon atoms, alkenyl of 2-7 carbon atoms, alkynyl of 2-7 carbon atoms, halogen, alkoxy of 1-4 carbon atoms, trifluoroalkyl of 1-6 carbon atoms, or trifluoroalkoxy of 1-6 carbon atoms; wherein the alkyl, alkenyl, or alkynyl moieties are each optionally substituted with one or more substituents independently selected from hydroxyl, —CN, halogen, trifluoroalkyl, trifluoroalkoxy, —COR$_5$, —CO$_2$R$_5$, —NO$_2$, CONR$_5$R$_6$, NR$_5$R$_6$ and N(R$_5$)COR$_6$;

$R_5$, $R_6$ are each, independently, hydrogen, alkyl of 1-6 carbon atoms, aryl of 6-10 carbon atoms; and X is O;

from a mixture comprising said compound and at least one impurity, comprising the steps of:
  a) recrystallizing said compound from a solution comprising acetone and acetonitrile to provide an initially purified product;
  b) dissolving said intially purified product in a solution comprising ethyl acetate;
  c) treating said solution comprising ethyl acetate with a clarifying agent to form a clarified solution;
  d) optionally concentrating said clarified solution to form a concentrated clarified solution or slurry;

e) adding a nonpolar solvent to said clarified solution or said clarified concentrated solution or slurry to form a mixed solvent solution or slurry; and
f) collecting the purified compound from said mixed solvent solution or slurry.

2. The process for claim 1 wherein said compound has the Formula I:

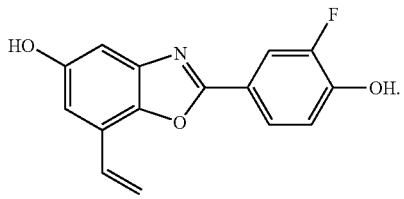

3. The process of claim 2 wherein step (a) comprises:
(i) dissolving said compound from said mixture in acetone to form a solution;
(ii) adding acetonitrile to the solution of step (i) to form a second solution; and
(iii) cooling the second solution.

4. The process of claim 3 wherein said dissolving of said step (i) is performed at a temperature greater than about 50° C.

5. The process of claim 3 wherein in step (ii):
the volume of acetonitrile added to said solution is from about 40% to about 65% of the volume of said solution; and
the acetonitrile is added to said solution while said solution is maintained at a temperature of greater than about 50° C.

6. The process of claim 3, wherein step (ii) further comprises concentrating said second solution to about one half its volume.

7. The process of claim 3, wherein step (iii) further comprises:
cooling said second solution to a temperature of from about 45° C. to about 50° C., and maintaining said second solution at about that temperature for about ten minutes or longer; and
further cooling of said second solution to a temperature of from about −10° C. to about 10° C., and maintaining said second solution at about that temperature for about an hour or longer.

8. The process of claim 7 further comprising:
filtering said second solution to collect an initially purified product; and
washing and optionally drying said initially purified product.

9. The process of claim 3 wherein:
said dissolving of said step (i) is performed at temperature of greater than about 50° C.;
in step (ii), the volume of acetonitrile added to said solution is from about 40% to about 65% of the volume of said solution;
in step (ii), the acetonitrile is added to said solution while said solution is maintained at a temperature of greater than about 50° C.;
step (ii) further comprises concentrating said second solution to about one half its volume;
step (iii) further comprises cooling said second solution to a temperature of from about 45° C. to about 50° C., and maintaining said second solution at about that temperature for up to about 45 minutes, and further cooling said second solution to a temperature of from about −10° C. to about 10° C., and maintaining said second solution at about that temperature for up to about 90 minutes;
and wherein said process further comprises filtering said second solution to collect a initially purified product, and optionally washing and optionally drying said initially purified product.

10. The process of claim 2 wherein:
in step (b), said initially purified product is dissolved in about 18 to about 28 volumes of ethyl acetate relative to the initially purified product at a temperature of from about 70° C. to about 90° C. to form an ethyl acetate solution; and
said treating of step (c) comprises:
contacting said solution comprising ethyl acetate with charcoal at elevated temperature to form a mixture, and filtering said mixture to provide said clarified solution; and
concentrating said clarified solution to about 5 volumes to about 10 volumes relative to said initially purified product to form a concentrated clarified solution or slurry.

11. The process of claim 2 wherein said adding of said nonpolar solvent of step (e) comprises adding from about 4 to about 8 volumes of said nonpolar solvent relative to the initially purified product at a temperature of from about 65° C. to about 90° C. to said concentrated clarified solution or slurry; and said nonpolar solvent comprises heptane.

12. The process of claim 2 wherein said nonpolar solvent of step (e) comprises heptane.

13. The process of claim 2 wherein said collecting of step (e) comprises cooling said mixed solvent solution or slurry to a temperature of from about 45° C. to about 50° C.;
maintaining said temperature for about ten minutes or longer;
further cooling said mixed solvent solution or slurry to a lower temperature of from about −10° C. to about 10° C. to form a cooled mixed solvent slurry; and
maintaining said lower temperature for about an hour or longer.

14. The process of claim 13 further comprising filtering said cooled mixed solvent slurry to collect said purified compound; and optionally washing and optionally drying said purified compound.

15. A process of purifying a compound of Formula I:

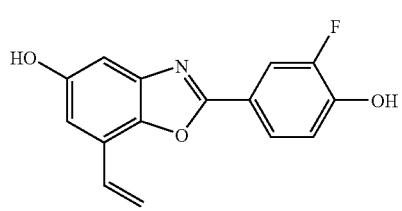

from a mixture comprising said compound and at least one impurity, comprising the steps of:
a) dissolving said compound from said mixture in acetone at elevated temperature to form a first solution;
b) adding to said first solution an amount of acetonitrile that is from about 40% to about 65% of the volume of said first solution, while maintaining said elevated temperature, to form a second solution;
c) concentrating said second solution to form a concentrated second solution;

d) cooling said concentrated second solution to form a precipitate of initially purified product;
e) collecting said initially purified product;
f) optionally washing and optionally drying said initially purified product;
g) dissolving said initially product in ethyl acetate at elevated temperature to form a third solution;
h) contacting said third solution with charcoal to form a mixture;
i) filtering said mixture to provide a clarified solution;
j) concentrating said clarified solution to form a concentrated clarified solution or slurry;
k) adding heptane to said concentrated clarified solution or slurry at elevated temperature;
l) cooling the concentrated clarified solution or slurry to form a mixed solvent solution or slurry; and
m) collecting the purified compound from the cooled further solution or slurry.

16. The process of claim 15, wherein:
the elevated temperature in step (a) is greater than about 50° C.;
in step (c), the second solution is concentrated to about half its volume; and
in step (d), the concentrated second solution is cooled said second solution to a temperature of from about 45° C. to about 50° C., and said second solution is maintained at about that temperature for about ten minutes or longer; and the concentrated second solution is further cooled to a temperature of from about −10° C. to about 10° C., and said second solution is maintained at about that temperature for about an hour or longer.

17. The process of claim 15, wherein:
in step (g), said initially product is dissolved in about 18 to about 28 volumes of ethyl acetate relative to the initially purified product at elevated temperature;
in step (h), said third solution is contacted with said charcoal at a temperature of up to about 50° C. to form said mixture;
in step (j), said clarified solution is concentrated to about 5 to about 7 volumes relative to said initially purified product at atmospheric pressure, to form said concentrated clarified solution or slurry;
in step (k), about 4 to about 8 volumes of heptane relative to the crude purified product is added to said concentrated clarified solution or slurry, at a temperature of up to about 90° C.; and
in step (l), said cooling of said concentrated clarified solution or slurry comprises:
  i) cooling said mixed solvent solution or slurry to a temperature of from about 45° C. to about 50° C. and maintaining said temperature for up to about 45 minutes after said cooling is complete; and
  ii) further cooling said mixed solvent solution or slurry to a temperature of from about −10° C. to about 10° C. and maintaining said temperature for up to about 90 minutes after said cooling is complete.

18. The process of claim 1 wherein the purity of said purified compound is about 99.0% or greater.

19. The process of claim 1 wherein the purity of said purified compound is about 99.2% or greater.

20. The process of claim 1 wherein the purity of said purified compound is about 99.4% or greater.

21. The process of claim 1 wherein the recovery of said compound from said mixture is about 80% or greater.

22. The process of claim 1 wherein the recovery of said compound from said mixture is about 83% or greater.

23. The process of claim 1 wherein the recovery of said compound from said mixture is about 86% or greater.

24. The process of claim 1 wherein the recovery of said compound from said mixture is about 89% or greater.

* * * * *

UNITED STATES PATENT AND TRADEMARK OFFICE
CERTIFICATE OF CORRECTION

PATENT NO. : 7,579,478 B2
APPLICATION NO. : 11/369113
DATED : August 25, 2009
INVENTOR(S) : Silvio Iera It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 454 days.

Signed and Sealed this

Fourteenth Day of September, 2010

David J. Kappos
*Director of the United States Patent and Trademark Office*